United States Patent [19]

Johnson et al.

[11] Patent Number: 4,953,387
[45] Date of Patent: Sep. 4, 1990

[54] ULTRATHIN-FILM GAS DETECTOR

[75] Inventors: Christy L. Johnson; Johannes Schwank; Kensall D. Wise, all of Ann Arbor, Mich.

[73] Assignee: The Regents of the University of Michigan, Ann Arbor, Mich.

[21] Appl. No.: 386,713

[22] Filed: Jul. 31, 1989

[51] Int. Cl.$^5$ ............................................. G01N 27/12
[52] U.S. Cl. ......................................... 73/25.03; 422/98
[58] Field of Search ................ 73/27 R, 23; 324/61 P; 422/98; 338/34

[56] References Cited

U.S. PATENT DOCUMENTS

| | | | |
|---|---|---|---|
| 3,714,562 | 1/1973 | McNerney | 338/34 X |
| 4,058,368 | 11/1977 | Svensson et al. | 73/23 X |
| 4,169,369 | 10/1979 | Chang | 73/23 |
| 4,224,280 | 9/1980 | Takahama et al. | 422/98 |
| 4,324,761 | 4/1982 | Harris | 422/98 |
| 4,338,281 | 7/1982 | Treitinger et al. | 422/98 |
| 4,343,768 | 8/1982 | Kimura | 422/97 |
| 4,347,732 | 9/1982 | Leary | 73/23 |
| 4,399,424 | 8/1983 | Rigby | 338/34 |
| 4,423,407 | 12/1983 | Zuckerman | 338/34 |
| 4,453,151 | 6/1984 | Leary et al. | 73/27 R X |
| 4,457,161 | 7/1984 | Iwanaga et al. | 73/23 |
| 4,482,882 | 11/1984 | Luder et al. | 338/34 |
| 4,510,036 | 4/1985 | Takeuchi et al. | 204/425 |
| 4,574,264 | 3/1986 | Takahashi et al. | 73/23 X |
| 4,580,439 | 4/1986 | Manaka | 73/23 |
| 4,587,105 | 5/1986 | Bonne et al. | 422/98 |
| 4,638,443 | 1/1987 | Kaneyasu et al. | 73/23 X |
| 4,661,234 | 4/1987 | Takahashi et al. | 338/34 X |
| 4,706,061 | 11/1987 | Johnson | 338/34 |
| 4,706,493 | 11/1987 | Chang et al. | 73/23 |
| 4,732,738 | 3/1988 | Nakatani et al. | 73/27 R X |
| 4,822,465 | 4/1989 | Jones et al. | 73/27 R X |

FOREIGN PATENT DOCUMENTS

| | | | |
|---|---|---|---|
| 0311439 | 4/1989 | European Pat. Off. | 73/23 |
| 3711071 | 10/1988 | Fed. Rep. of Germany | 73/23 |
| 75249 | 4/1986 | Japan | 73/23 |

Primary Examiner—Hezron E. Williams
Assistant Examiner—Joseph W. Roskos
Attorney, Agent, or Firm—Oblon, Spivak, McClelland, Maier & Neustadt

[57] ABSTRACT

A device for detecting a gaseous species including (i) a silicon substrate having two major surfaces and comprising a dielectric window region (ii) a heater situated on the dielectric window region on one major surface; and (iii) a conductivity cell electrode thin metal transducing film assembly situated on the dielectric window region on the other major surface is disclosed. The thin transducing film contacts the conductivity cell electrode.

27 Claims, 8 Drawing Sheets

ULTRATHIN-FILM GAS DETECTOR

BACKGROUND OF THE INVENTION

1. Field of the Invention

The invention relates to gas sensors.

2. Discussion of the Background

Gas sensors are useful for safety monitoring, process monitoring and control, evaluation of gaseous product quality, environmental control and automotive applications ranging from analysis of (i) engine air-to-fuel ratios, (ii) exhaust, (ii) passenger's compartment, and (iii) to breath tests. There is a significant need for inexpensive, selective and reliable gas sensors for performing these functions.

It is known to detect a species in a composite gas using a thin film of a suitable semiconductor material whose electrical resistivity changes in response to a presence of the species. For example, a semiconductor tin oxide thin film may be used to detect nitrogen oxides $NO_x$. See U.S. Pat. No. 4,169,369. The electrical resistance of the film exposed to the gas is measured and provides a basis for determining the concentration of the species. The responsiveness of the film is temperature dependent. In general, it is necessary to heat the film to a predetermined elevated temperature to optimize the sensitivity for the particular species.

The delicate thin film is carried on a substrate having a substantially greater thickness to permit convenient handling. It has been proposed to mount a plurality of semiconductor thin films on a common substrate. For example, a second film may be employed to detect interference due to a species other than the primary species of interest. The films, which may have like or unlike compositions, may have distinct sensing temperatures.

The substrate may also include an integrated circuit for interpreting the electrical resistance measurements, the operation of which may be adversely affected by heat. To better control temperature at other sites of the sensor, it is desired to limit the heating of the film to the immediate location of the film. However, heating the film necessarily results in heat loss to the underlying substrate, which tends to conduct heat to other locations of the device.

U.S. Pat. No. 4,706,493 discloses a gas sensing device having a tin oxide thin film deposited onto a silicon dioxide layer overlying a heating element. This tin oxide thin film comprises a gas contact surface carrying a thin, discontinuous palladium-gold catalytic film to enhance sensitivity. In this device the tin oxide film is the situs of the gas detection region of the device.

To date, however, gas sensing devices have not been very selective and frequently show failure mechanisms that preclude long term use. In particular, devices based on film conductivity, including $SnO_x$ devices, have the following problems: low sensitivity (ability to detect gas of interest) and failure to quantify gas present, low selectivities (ability to detect the gas of interest in the presence of other gases), long-term drift, hysteresis effects, limited range of gases that can be detected, limited range of operating temperature and slow responses.

Accordingly, there is a strongly felt need for a gas detector which does not suffer these disadvantages.

SUMMARY OF THE INVENTION

Accordingly, it is an object of this invention to provide a gas detecting device which selectively and sensitively detects gases with a rapid response and essentially no hysteresis or drift.

It is another object of this invention to provide a gas detecting device capable of detecting and quantifying a plurality of different constituents in a multicomponent gas.

It is another object of this invention to provide a gas detecting device wherein temperatures on the devices can be rapidly cycled across a broad range resulting in very good sensing and control.

These and other objects are achieved according to the present invention which provides a new and improved device for detecting gaseous species. This device includes a substrate having two opposed major surfaces, a dielectric window region, a heater situated on the dielectric window region on one of the opposed major surfaces, and a set of conductivity cell electrodes/thin transducing metal film assembly situated on the dielectric window region on the other of the opposed major surfaces. The thin transducing film contacts the conductivity cell electrode means.

The set of conductivity cell electrodes/thin transducing metal assembly, in one preferred embodiment, is replaced by a first set of conductivity cell electrodes/thin transducing metal film/second set of conductivity cell electrodes assembly.

BRIEF DESCRIPTION OF THE FIGURES

A more complete appreciation of the invention and many of its attendant advantages will be readily obtained as the same becomes better understood by reference to the following detailed description when considered in connection with the accompanying figures, wherein.

DETAILED DESCRIPTION OF THE PREFERRED EMBODIMENTS

Three embodiments for the set of conductivity cell electrodes/thin transducing metal film assembly are provided by the present invention.

Figure 1A:
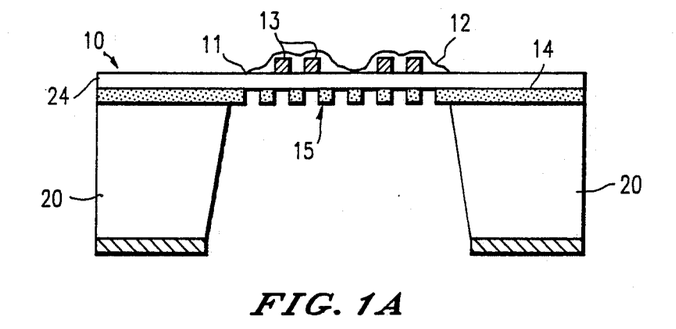
FIG. 1a provides a cross sectional view of the device.
Figure 1B:
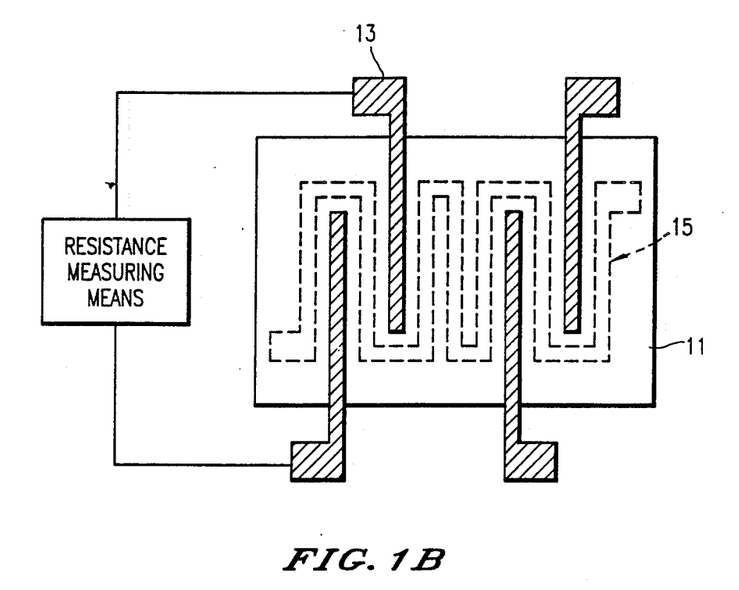
FIG. 1b provides a top view of the dielectric window of the device.

In a first embodiment (illustrated in FIG. 1), the set of conductivity cell electrode means (13) are sandwiched between the dielectric window region (11) and the thin transducing metal film (12).

In a second embodiment (illustrated in FIG. 6a), the thin transducing metal film (12) is sandwiched between the set of conductivity cell electrode means (13) and the dielectric window region (11).

In a third embodiment (illustrated in FIG. 6b), an assembly made up of a first set of conductivity cell electrodes (13)/thin transducing metal film (12)/a second set of conductivity cell electrodes (22) assembly is used. In this third embodiment, the dielectric window region supports a first set of conductivity cell electrodes which are in turn covered by the thin transducing metal film which itself supports the second set of conductivity cell electrodes.

The present device can be used with a broad range of gas sensing. The device is easily fabricated, using standard semiconductor batch processing. Fabrication requires the use of only five simple masking steps. Yield of the devices is very high and thus the devices are inexpensive to produce.

The present invention employs thin film technology. Many devices are based on semiconductor films, such as tin oxide (e.g., U.S. Pat. Nos. 4,706,493 or 4,169,369), that involve surface adsorption, diffusion of the gas through the bulk of the film and finally an electrical response. This is not only a slow process, it also can cause irreversible structural changes within the sensing film resulting in deterioration of device performance. Others have used some thin films in conjunction with FET devices but these are much more complex from a fabrication standpoint and can only be used over a limited temperature range.

Referring now to the figures, wherein like reference numerals designate identical or corresponding parts throughout the several views, and more particularly to FIGS. 1a and 1b thereof, FIG. 1a and 1b provides a cross-sectional view and a top view, respectively, of one embodiment of the basic device structure (10). A substrate (24) comprises a selectively micromachined dielectric window (11) which supports a transducing thin metal film (12) and an array of conductivity cell electrodes (13). The transducing thin metal film (12) is in electrical contact with the conductivity cell electrodes (13).

The cell electrodes (13) are used to sense the film's conductivity and capacitance. The thin film resistance and capacitance measurements can be performed with two, three or four electrodes. The two electrode case is the least accurate of the three as the contact resistance is included in the measurement and is a significant fraction of the overall resistance. In this case, the same two electrodes are used for both current application and voltage measurement.

Accuracy is improved with three electrodes as the contribution of the contact resistance to the overall resistance is reduced. For a three-point measurement, one of electrodes is grounded and then current is sent between a second electrode and the grounded electrode and the voltage is measured across the grounded electrode and the other non-grounded electrode.

Further improvement is seen with a four electrodes configuration (illustrated in FIG. 1b). Here current is sent through the two outer electrodes and the voltage is measured across the two inner electrodes. Additional redundant electrodes may be included on-chip in case of electrode failure (i.e., bond failure) but more than four electrodes does not appreciably further improve accuracy.

The sensor features the thin-diaphragm dielectric window (11) in the center of the chip. A heater means (15) below this window allows rapid temperature cycling of the device, in particular of the dielectric window (11) and the ultrathin film (12). The substrate (24) may be advantageously designed with support means (20).

Figure 6A:
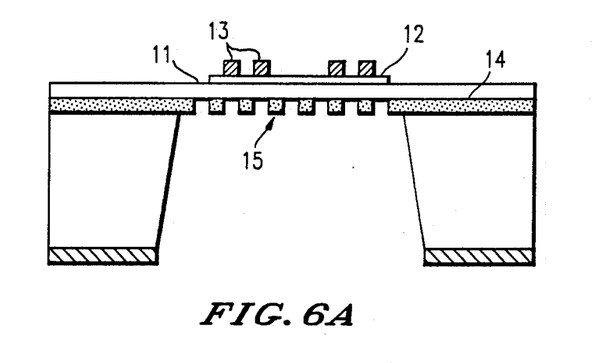
FIGS. 6a and 6b provide a cross sectional view of modifications of the device.

In the second embodiment, illustrated in FIG. 6a, the thin film (12) is sandwiched between the dielectric window (11) and the conductivity cell electrode means (22). This structure improves the contact between the thin film (12) and the conductivity cell electrodes (13) as compared to the embodiment, illustrated in FIG. 1, of thin film placement following conductivity cell electrode means definition. However, with some films with poor adhesion to the oxide, adhesion problems may arise especially in the conductivity cell electrode areas. Adhesion can be improved by adding an adhesion prompting film below the electrode region or underneath the entire thin film region.

Figure 6B:
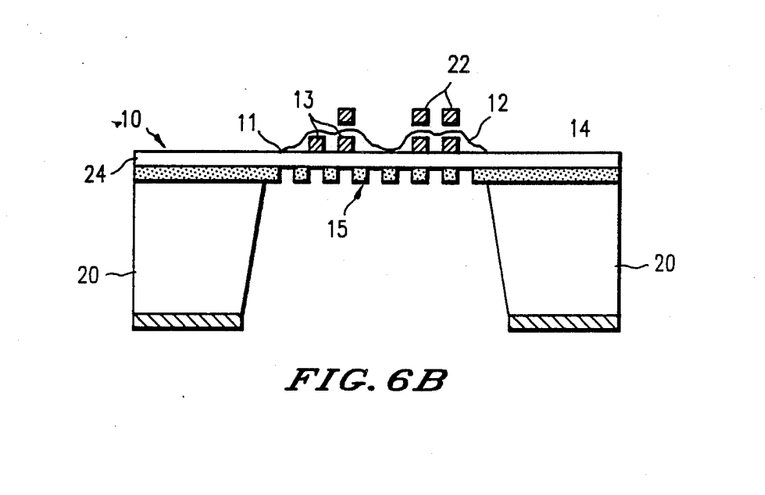

In the embodiment illustrated in FIG. 6b good physical contact is obtained by adding a second set of conductivity cell electrode means (22) over the thin film (12) thus forming a sandwich comprised of the first conductivity cell electrode means (13), the thin metal particle film (12), and the second conductivity cell electrode means (22).

The substrate (24) and the dielectric window (11) of the present device comprises a $SiO_2/Si_3N_4/SiO_2$ dielectric sandwich in mild tension. The thickness of these, measured as the ratio of the total thickness of the silicon oxide layers to the thickness of the silicon nitride layer, is greater than 1:1, preferably greater than 2.5:1, and up to 6:1.

A layer or combination of layers of insulators, metals or semiconductors can be added on top of the $SiO_2$ to modify film sensitivity, to improve adhesion and/or to protect the oxide from a harsh environment. One example is the case of using a Ti layer below a Pt layer. In addition to improving adhesion to the $SiO_2$, the Ti/Pt system sensing behavior differs from Pt alone. In addition, the Ti film can be irreversibly oxidized to a $TiO_x$ semiconducting film. The Pt film alone should sense only $O_2$, the Ti plus Pt film should sense both $O_2$ and $H_2$ and the $TiO_x$ plus Pt should sense only $H_2$.

The metal of the transducing thin metal film (12) may be platinum, palladium, ruthenium, nickel, copper, rhodium, molybdenum, iridium, iron, cobalt, titanium, vanadium, tantalum, tungsten, chromium, manganese, gold, aluminum, tin, magnesium, osmium, zinc, silver or a combination of two or more of these. Of these metals, platinum, palladium, ruthenium, nickel, copper, rhodium, molybdenum, iridium, iron, cobalt, titanium, vanadium, tantalum, tungsten, chromium, manganese, gold, and silver are preferred.

The thickness of the transducing thin metal film (12) is from 0.5 nm to 25 nm, preferably 5 nm to 10 nm. At these thicknesses the film may be described as contacting the conductivity cell electrode means as an essentially continuous film. Depending on film thickness the film may contain some areas of discontinuity.

The resistance of the thin film should be 10 ohms to $10^7$ ohms. Preferably it is $10^3$ ohms to $10^4$ ohms.

In another embodiment of this invention, a discontinuous layer of a material capable of selectively removing one component from the multi-component gaseous mixture is situated on top of the thin metal transducing film (12). Materials, known as molecular sieves, can be spun on or deposited from solution and allowed to dry to obtain films which are especially effective in molecular size separation as the pore size of the sieve determines whether a molecule will be able to pass through the sieve and reach the sensing surface. Such materials include zeolites which can be used to selectively remove water from a gaseous mixture. This embodiment may be advantageously used to remove a component which otherwise prevents detection of a second component in a multi-component gaseous mixture.

Since the transducing thin metal film (12) is very thin, it is important that the upper surface of the dielectric window (11) be substantially planar to avoid step coverage problems. Accordingly, in an advantageous embodiment a boron diffusion may be used to form both the rim (14) next to the dieletric window (11) and the resistive heater means (15) under it. The rim (14) eliminates front-back alignment problems, while the bulk-diffused heater means (15) maintains the planarity of the window (11) in a way not possible using polysilicon structures. Large heater contact areas minimize the thermal effects on this region.

The transducing thin metal film (12) may be deposited after the final silicon etch and die separation to avoid compatibility problems with the silicon etch and for additional flexiblity of sensor film on a given wafer. Shadow masking may be used to allow selective localization of the transducing area.

The conductivity cell electrode means (13) or (22) may be made of chrome/gold electrodes, or preferably, if the device is to be used at high temperatures, these electrodes may be made of a refractory material such as tantalum, titanium and iridium-containing materials or refractory metal silicides.

Figure 2:
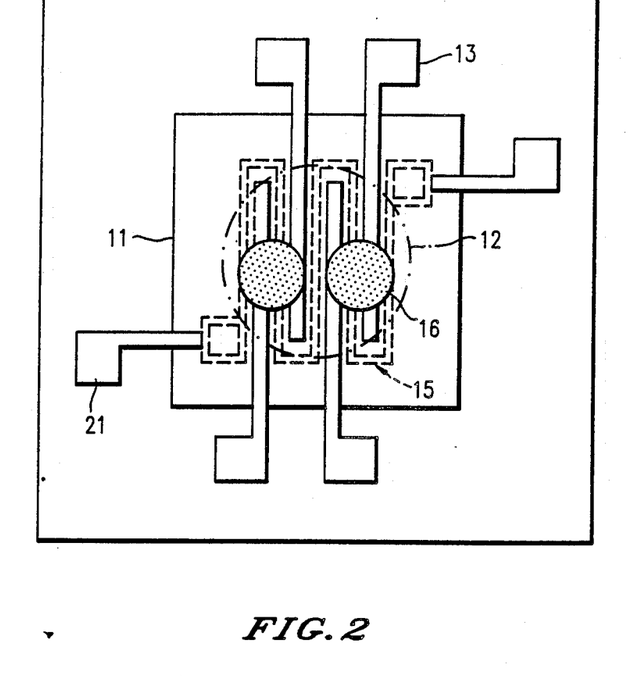
FIG. 2 provides a top view of a modification of the device.

As illustrated in FIG. 2, in another embodiment, good physical contact with the transducing thin metal film (12) may be obtained by evaporating an additional two circles of metal (16) (e.g. Au, Ta, Ir, Al) on each side of the device, thereby forming a sandwich of the original conductivity cell electrodes (13), the ultrathin metal particle film (12) and another layer of metal (16). This figure also illustrates (21) heater contact means.

Figure 9:
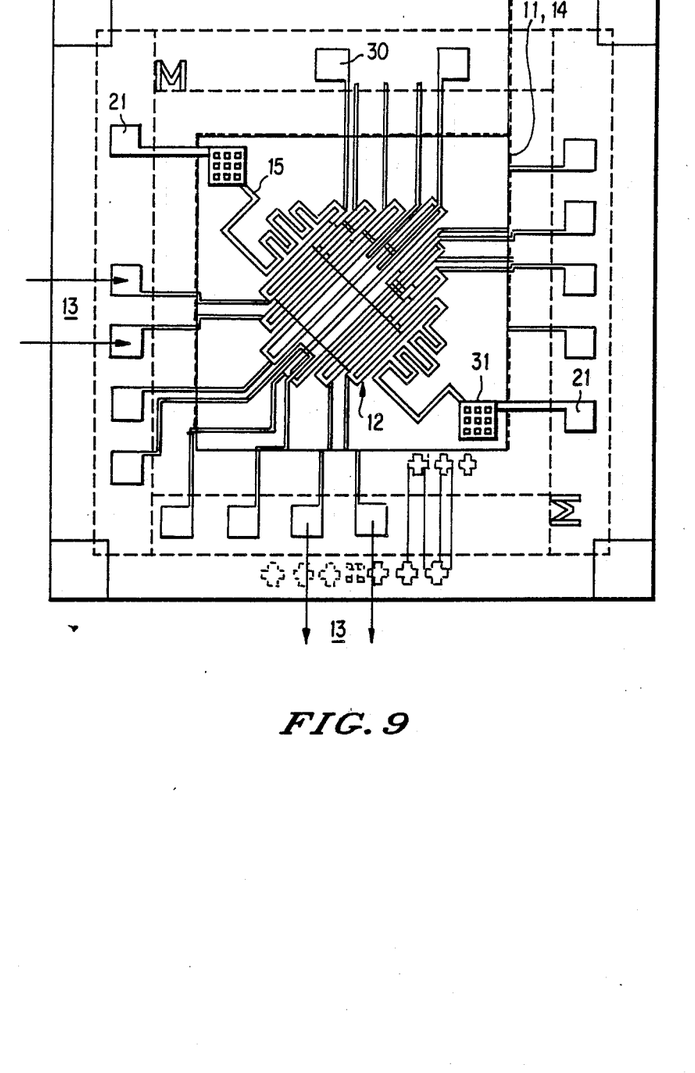
FIG. 9 provides a top view of one of the preferred embodiments of the present invention.

FIG. 9 provides a top view of the configuration of a preferred embodiment of the present invention. The device of FIG. 9 illustrates a particular heater (15) design which provides improved temperature distribution across window (11), contacts (31), and a thermopile (30) for independent temperature measurement.

OPERATION OF THE DEVICE

The detector of this invention has a significantly simpler operating process and requires less input power than previously reported designs. The principle on which the device is based is also different.

It is known from catalysis that a given gas has a characteristic temperature at which it will desorb from a given metal. These characteristics can be utilized to:

(a) identify the gas through its induced desorption; and (b) to remove possible unwanted species by ramping the temperature above the temperature at which desorption occurs.

In light of this there are two possible modes of operation for the device heater. In the first mode, the heater current is held constant and changes in gaseous environment cause changes in the heater resistance and in the device temperature. These induced changes are dependent upon the amount and the thermal conductivity of the gases present and may be used to identify and quantify the presence of a gas.

This phenomena is the basis for two well-known pressure gauges; the Pirani gauge and the thermocouple gauge. Interestingly, the cited drawbacks to these gauges is the species specificity due to thermal conductivity differences which is actually advantageous in gas sensing. A drawback of this mode is that both thermal and chemical events may be occurring simultaneously and they are difficult to decouple in this mode.

In the second operating mode, the heater resistance and temperature are held constant by adjusting the amount of current through the heater. Thermal information about the gases present is obtained from the magnitude of the required current adjustment needed to maintain the desired temperature and the chemical information is obtained from the thin film resistance and capacitance changes.

Gas adsorption and possible surface reaction on the transducing thin metal film changes its resistance and capacitance. The resulting changes are used to generate an output voltage dependent on the type and quantity of gas present, thus permitting detection and identification of the gas.

Figure 7A:
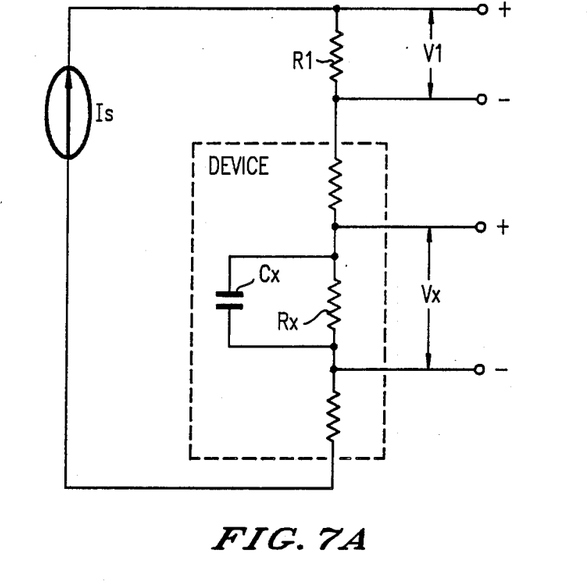
FIGS. 7a and b illustrate circuits which may be used with the present device to detect a gas (7a=4-point measurement; 7b=2-point measurement)
Figure 7B:
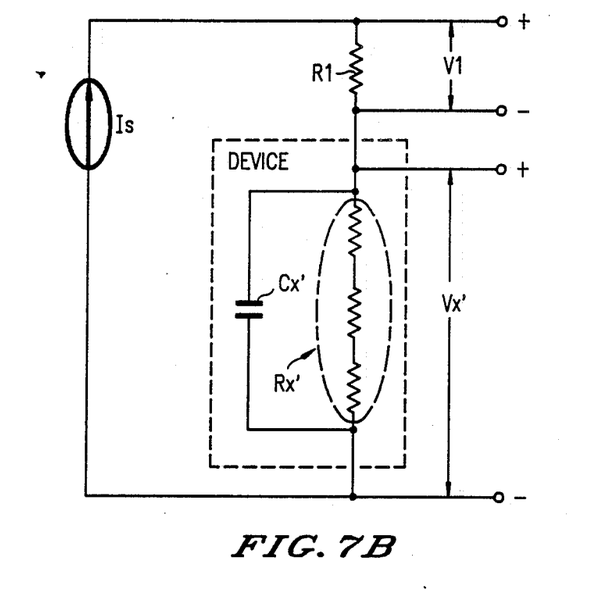

In the case of a two-point probe, illustrative equivalent circuits which may be used is diagrammed in FIGS. 7a and b. The first measured parameter is the voltage drop, $V_1$, across the known resistor, $R_1$. The source current is then calculated from $$I_s = (V_1/R_1) \tag{2}$$

If dc current is used, the unknown device resistance is calculated from $$R_x = (V_x/I_s) \tag{2}$$

The dc case provides no information on the capacitance of the device.

For ac current, the total impedance of the device, $Z_x$, which includes the parallel contribution of the thin film resistance and capacitance, is obtained from the voltage drop $V_x$ across the device and the series current $I_s$, $$Z_x = (V_x/I_s) \tag{3}$$

The impedance is a function of the parallel resistance and capacitance of the device as follows:

$$Z_x = [R_x/(j\omega R_x C_x + 1)] \tag{4}$$

where $\omega = 2\pi\nu$ and $\nu$ is the frequency of the input current. The phase shift, $\phi$, is also a function of $R_x$ and $C_x$:

$$\Omega = tan^{-1}[\omega R_1 R_x C_x/(R_1 + R_x)] \tag{5}$$

Equations 4 and 5 are then used to solve for the unknown values of $R_x$ and $C_x$.

The difference between the two-point measurement (FIG. 7b) and the four-point probe measurement (FIG. 7a) lies in the location of the conductivity cell electrodes where the unknown voltage is measured. This is shown in the circuit illustrated in FIG. 7.

Part of the device resistance, including a significant amount of the contact resistance can be essentially ignored by just measuring across two inner electrodes. The calculation of resistance and capacitance is identical to that shown for the two-point case.

Gas adsorption on the surface of the transducing thin metal film alone may change the ability of current to flow through the conductivity cell electrodes means, thereby causing a change in resistance and/or capacitance. This change can then be correlated to the gas type and the concentration of gas, even in the presence of other gases. Since this is only a surface change, the response is rapid and structural changes in the film are dramatically lessened.

A calibration curve for device resistance and capacitance and for required heater current adjustments as a function of temperature and pressure and input frequency for each gas and thin film is first obtained. In the ideal case, introduction of a given pressure of a gas will cause a characteristic resistance and capacitance change of the thin film and thus the gas can be identified on the basis of this measurement.

If a single data point does not provide enough information to identify and quantify the gas, the device temperature and/or input frequency can be cycled or the total pressure changed by the addition or removal of some gas and more measurements taken. Again, this is compared to the calibration curves for a positive identification and quantification.

It is possible that different gases may cause the same resistance changes on a given thin film or that a combination of gases could confound the measurement by interactive effects. This is when temperature programmed desorption becomes important. A given gas desorbs at a characteristic temperature from the thin film in question. The temperature is ramped to this temperature to induce this desorption. A resistance or capacitance change occurs after removal of the gas if it is indeed present and also allows any other species that were blocked from adsorption at lower temperatures to adsorb and be sensed.

In the event that there still is not a sufficient amount of information to identify and quantify the gas, the sequence may be repeated with a different thin film until all the constituents of the mixture have been identified and quantified. This is one of the advantageous uses of the array of sensors provided by the invention where the number of sites in the array is determined by the sensitivities and selectivities of the individual films to the gases to be sensed and the gases in question.

If a failure occurs, treatments at high temperatures in a suitable atmosphere can be used to recover original structure and original device performance. For example, the atmosphere used can be a reducing atmosphere if reducing on the metal surface is desired. The atmosphere can be an oxidizing atmosphere if oxidation of the surface is desired. And the atmosphere may be inert if it is desired to simply free the surface of contaminants.

From a given wafer, hundreds of different gas sensors can be fabricated depending upon the transducing films chosen. In another embodiment, illustrated in FIG. 4, the present detector may be used to form one cell in a multi-element gas analyzer chip (19) in which a plurality of dielectric windows (11) are each coated with a different thin metal film material and equipped with an independent heater control means. In this embodiment heater/detection circuit means (18) and ADC/interface circuit means (17) are provided.

Figure 4:
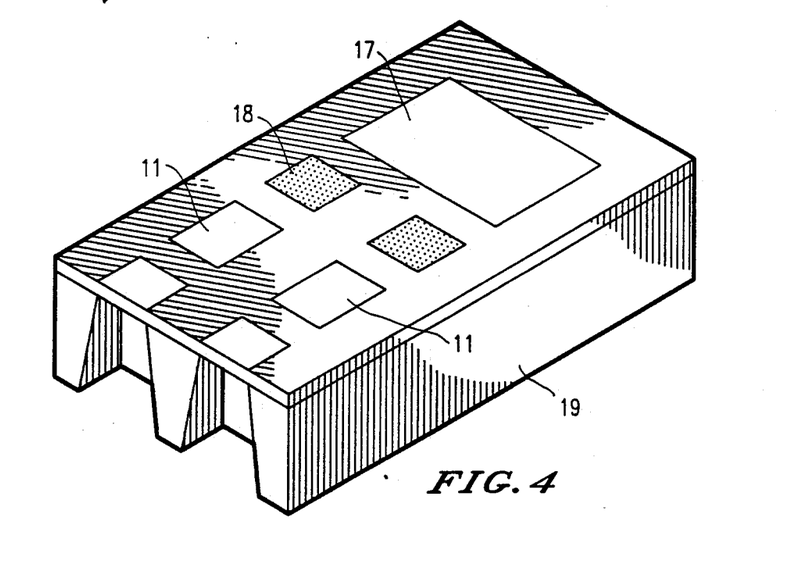
FIG. 4 illustrates a multi-element sensor array with thermally isolated windows and circuitry.

With this design different responses from each of the windows in the presence of individual gases, or gaseous mixtures, allows response profiles to be derived. These characteristic profiles are then used to enhance the device's selectivity and sensitivity to a variety of gases. In addition, temperature-programmed desorption can be used for additional selectivity and control.

Other features of this invention will become apparent in the course of the following descriptions of exemplary embodiments which are given for illustration of the invention and not intended to be limiting thereof.

Illustrative Manufacture and Operation of the Present Device

A (100) oriented silicon wafer is patterned with photolithography on both sides to define boron diffusion regions that will define the size of the diaphragm window (11) and the recessed heater means (15). Diffusion is followed by thermal oxidation, and chemical vapor deposition nitridation and oxidation to form three dielectric layers. These three dielectric layers eventually form the window (11) in mild tension.

Opening of the contacts to the heater below the window is next followed by metal deposition of chromium and gold or other suitable metals to define both the contacts to the heater (15) and the conductivity electrodes (13) used for gas sensing. The dielectrics formed on the backside of the wafer are removed and the wafer is immersed in anisotropic EDP (ethylenediamine pyrocatechol) which etches silicon but not highly p-doped regions, dielectrics or metal electrodes. This defines the window area and leaves it thermally isolated from the rest of the device. The etch also allows separation of the individual sensors from the wafer itself.

The final stage is the deposition of the thin metal particle film (12) on the surface of each sensor. This allows for greater flexibility in choice of transducing films and film thickness. The thin films may be flash evaporated through a shadow mask over the sensors. The transducing thin metal film may also be applied by sputtering. Either of these approaches allows selective placement of the film. However, this invention is not limited to thin films formed by flash evaporation or sputtering. The thin film may be formed by any suitable method, depending on the nature of the material used to make the film.

Figure 5A:
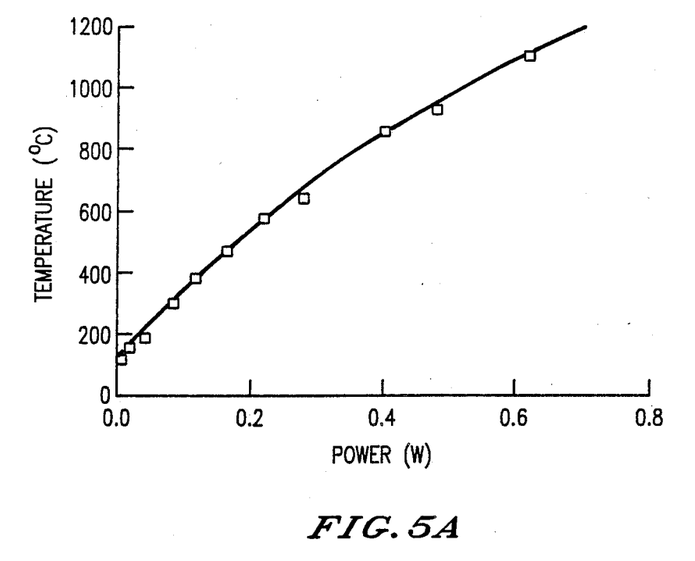
FIG. 5a illustrates measured diffused heater temperature characteristics with respect to power.
Figure 5B:
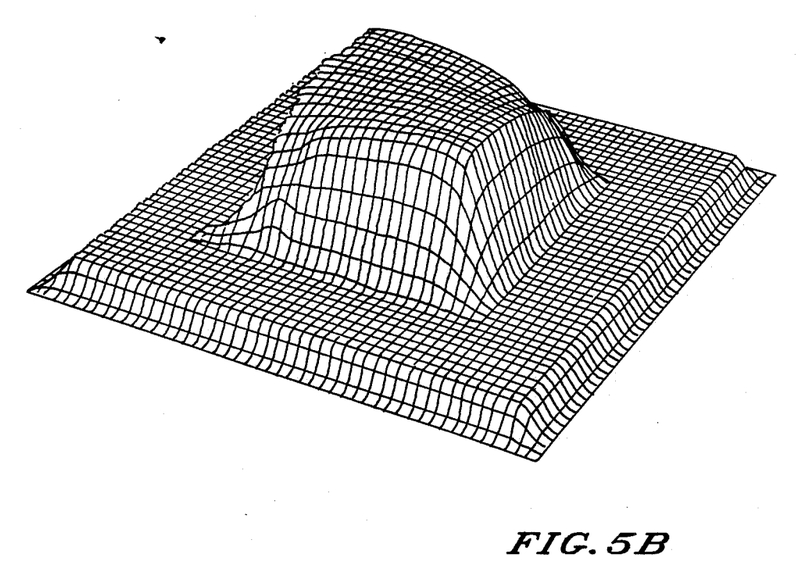
FIG. 5b illustrates simulated detector window temperature.

Exemplary heater means characteristics and a simulation of the temperature distribution over the window are provided in FIGS. 5a and 5b. Upon completion of the silicon etch, the heater means was 5 $\mu$m deep with a resistance of about 500 ohms at room temperature. The dielectric windows were heated with an efficiency of about 3° C./mW and had a thermal time constant of about 10 msec. The heaters had been cycled to temperatures exceeding 1000° C. without difficulty, although for continuous operation at such extreme temperatures, a different electrode metallization system (e.g., tantalum) should be used.

For example, the sensors may be fabricated with a Ti/Ir refractory system and the heaters and heater contacts are stable at 1000° C. One heater was at 1000° C. for 20 minutes and its performance did not change. As an aside, the sensors will probably only be ramped up to high temperatures for short periods of time to do temperature programmed desorption experiments.

Figure 3:
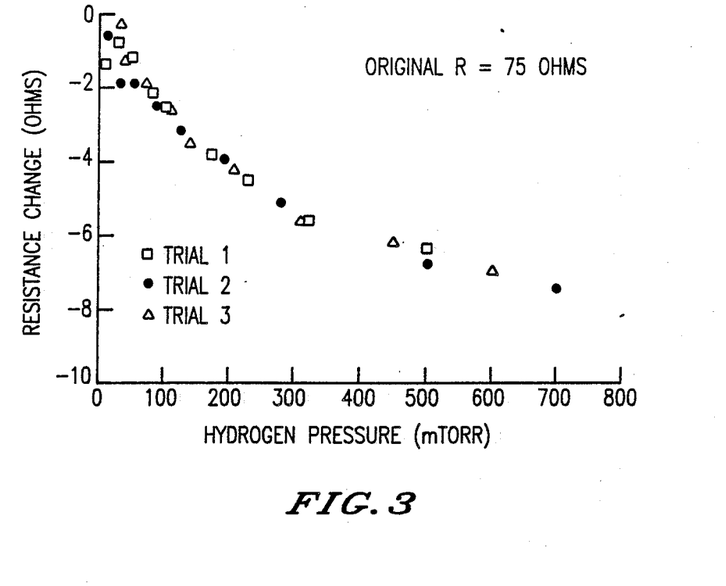
FIG. 3 illustrates sensor response to hydrogen at constant heater current.

FIG. 3 shows the response of one device to the introduction of pressures from 0 to 800 mTorr for "pure" hydrogen with a 8.5 nm-thick Pt sensing film tested at constant heater current. This figure shows a resistance change of a 8.5 nm Pt film vs. pressure of hydrogen plot that demonstrates the ability of the sensor not only to detect gases but also to quantify them. Gas sensitivity as a function of temperatures increases for higher temperatures in the pressure range noted.

The sensor also detected trace amounts of oxygen (250 ppm) in the presence of high concentrations of the fluorocarbon (200 mT). Detection of parts per million of reactive ion etching process gases were the original target of the work and our work shows that there was no response to $CF_4$ at the pressures commonly used in RIE processing. However, and this is one of the significant aspects of this device, parts per million of oxygen in the presence of the fluorocarbon were detected and can be quantified.

The response is linear with oxygen concentrations in the ppm range. The device's high selectivity for $O_2$ in the presence of $CF_4$ simplifies sensing for $O_2$ in a $CF_4$ atmosphere since the major constituent can essentially be ignored while analyzing for ppm impurities of $O_2$.

The device has shown no noticeable drift or hysteresis on repeated temperature cycling. The response time is on the order of 1 second since the device operates based strictly on surface effects, and is substantially faster than existing gas sensors, which rely on diffusion of the gas throughout the bulk of the film and as a result respond in minutes.

Figure 8:
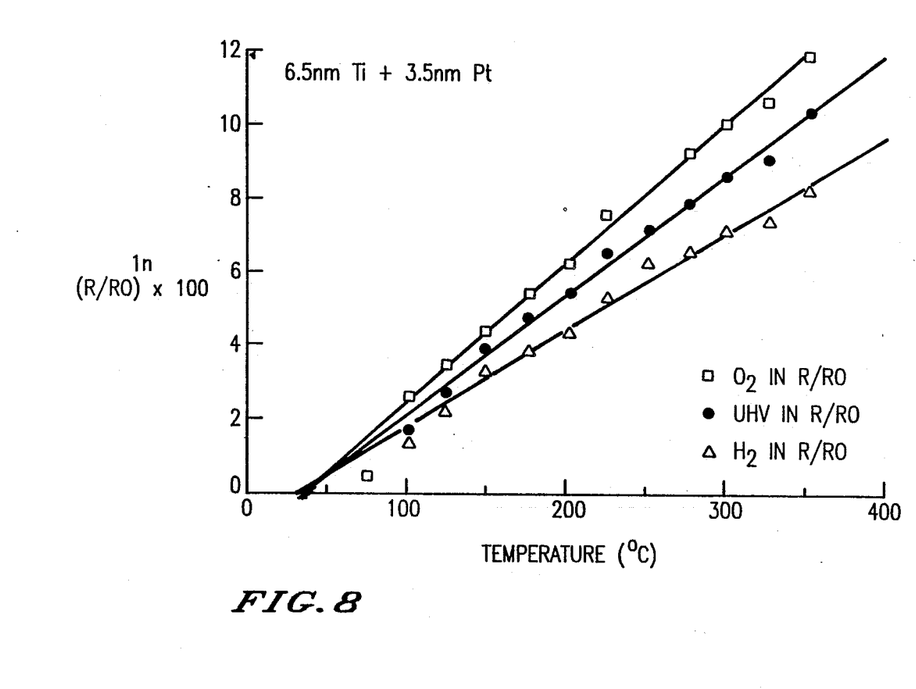
FIG. 8 provides a graph showing discrimination between two components in a gas on the basis of gas chemistry.

FIG. 8 provides a $\ln(R/R_O)$ vs. temperature graph that shows the ability of a device equipped with a 6.5 nm Ti plus 3.5 nm Pt film to discriminate between two different gases on the basis of the gas chemistry. Constant temperature operating mode was used.

The graph shows a relation of resistance (R) to initial resistance ($R_0$) as a function of device temperature. The upper curve is for the case of 80 mT $O_2$ and the lowest for 700 mT $H_2$. The intermediate curve is of temperature cycling in ultra-high vacuum (i.e., very low gas concentration) which essentially shows the temperature coefficient of resistance of the thin film itself. The results are as expected with $O_2$ apparently causing an oxidation event resulting in more insulating behavior (higher resistance) and the $H_2$ apparently causing a reduction event or more metallic behavior (lower resistance).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for detecting a gaseous species, comprising:
    (i) a substrate having two opposed major surfaces and including a dielectric window region;
    (ii) heater means situated on said dielectric window region on one of said opposed surfaces; and
    (iii) a conductivity cell electrode means/thin transducing metal film assembly situated on said dielectric window region on the other of said opposed surfaces;
    wherein:
    said thin transducing metal film contacts said conductivity cell electrode means;
    said heater means heats said thin transducing film; and
    said conductivity cell electrode means senses the conductivity and capacitance of said thin transducing film.

2. The device of claim 1, wherein said metal film is at least one member selected from the group consisting of platinum, palladium, ruthenium, nickel, copper, rhodium, molybdenum, iridium, iron, cobalt, titanium, vanadium, tantalum, tungsten, chromium, manganese, gold, aluminum, tin, magnesium, osmium, zinc and silver.

3. The device of claim 1, wherein said thin transducing metal film has a thickness of 0.5 nm to 25 nm.

4. The device of claim 1, wherein said thin transducing metal film has a thickness of from 5 nm to 10 nm.

5. The device of claim 1, wherein said thin transducing metal film has a resistance of from 10 ohms to $10^7$ ohms.

6. The device of claim 1, wherein said thin transducing metal film has a resistance of from $10^3$ ohms to $10^4$ ohms.

7. The device of claim 1, wherein said conductivity cell electrode means are chrome/gold electrodes.

8. The device of claim 1, wherein said conductivity cell electrode means are made of a refractory material such as Ir, Ta or Ti.

9. The device of claim 1, wherein said heater means is a polysilicon heater means.

10. The device of claim 1, wherein said heater means is a boron-doped silicon heater means.

11. The device of claim 1, wherein said substrate is a laminate comprising a silicon nitride layer sandwiched between two silicon oxide layers.

12. The device of claim 11, wherein the substrate has a thickness in which the total silicon oxide to silicon nitride ratio is at least 1:1.

13. The device of claim 12, wherein said ratio is from 2.5:1 to 6:1.

14. A device for detecting a gaseous species, comprising:
    (i) a substrate having two opposed major surfaces and including a dielectric window region;
    (ii) a heater means situated on said dielectric window region on one of said opposed surfaces;
    (iii) a first set of conductivity cell electrode means/thin transducing metal film/second set of conductivity cell electrode means assembly situated on said dielectric window region on the other of said opposed surfaces;
    wherein:
    said second-thin transducing metal film contacts said first and said second set of conductivity cell electrode means;
    said heater means heats said thin transducing metal film; and
    said first and second conductivity cell electrode means sense the conductivity and capacitance of said thin transducing metal film.

15. The device of claim 14, wherein said thin transducing metal film has a thickness of 0.5 nm to 25 nm.

16. The device of claim 14, wherein said thin transducing metal film has a thickness of from 5 nm to 10 nm.

17. The device of claim 14, wherein said thin transducing metal film has a resistance of from 10 ohms to $10^7$ ohms.

18. The device of claim 14, wherein said thin transducing metal film has a resistance of from $10^3$ ohms to $10^4$ ohms.

19. The device of claim 14, wherein said conductivity cell electrode means are chrome/gold electrodes.

20. The device of claim 14, wherein said conductivity cell electrode means are made of a refractory material such as Ir, Ta or Ti.

21. The device of claim 14, wherein said heater means is a polysilicon heater means.

22. The device of claim 14, wherein said heater means is a boron-doped silicon heater means.

23. The device of claim 14, wherein said substrate is a laminate comprising a silicon nitride layer sandwiched between two silicon oxide layers.

24. The device of claim 23, wherein the substrate has a thickness in which the total silicon oxide to silicon nitride ration is at least 1:1.

25. The device of claim 24, wherein said ratio is from 2.5:1 to 6:1.

26. A multi-element gas analyzer chip, comprising:
(i) a substrate having two opposed major surfaces and including a plurality of dielectric window regions;
(ii) heater means situated on each of said dielectric window region on one of said opposed surfaces; and
(iii) a set of conductivity cell electrode means/thin transducing metal film assembly situated on each of said dielectric window region on the other of said opposed surfaces;

wherein:
each thin transducing metal film contacts each corresponding set of conductivity cell electrode means;
each of said heater means independently heats each corresponding thin transducing metal film;
each of said conductivity cell electrode means senses the conductivity and capacitance of said corresponding transducing thin metal film.

27. A multi-element gas analyzer chip, comprising:
(i) a substrate having two opposed major surfaces and including a plurality of dielectric window regions;
(ii) heater means situated on each of said dielectric window region on one of said opposed surfaces; and
(iii) first set of conductivity cell electrode means/thin transducing metal film/second set of conductivity cell electrode means assembly situated on each of said dielectric window region on the other of said opposed surfaces;

wherein:
each thin transducing film contacts each corresponding set of conductivity cell electrode means;
each of said heater means independently heats each corresponding thin transducing metal film;
each of said conductivity cell electrode means senses the conductivity and capacitance of said corresponding transducing thin metal film.

* * * * *